United States Patent
Wong et al.

(10) Patent No.: US 11,649,349 B2
(45) Date of Patent: May 16, 2023

(54) THERMOPLASTIC ELASTOMERIC FORMULATION

(71) Applicant: Top Glove International Sdn. Bhd., Klang (MY)

(72) Inventors: Chong Ban Wong, Klang (MY); Keuw Wei Lim, Klang (MY); Arman Sikirman, Klang (MY); Chee Kin Phang, Klang (MY); Nurjihan Sadon, Klang (MY)

(73) Assignee: Top Glove International Sdn. Bhd.

( * ) Notice: Subject to any disclaimer, the term of this patent is extended or adjusted under 35 U.S.C. 154(b) by 270 days.

(21) Appl. No.: 17/070,588

(22) Filed: Oct. 14, 2020

(65) Prior Publication Data
US 2021/0122913 A1  Apr. 29, 2021

(51) Int. Cl.
*C08L 53/02* (2006.01)
*A61B 42/10* (2016.01)

(52) U.S. Cl.
CPC .............. *C08L 53/02* (2013.01); *A61B 42/10* (2016.02)

(58) Field of Classification Search
CPC ...................................................... A61B 42/10
See application file for complete search history.

(56) References Cited

U.S. PATENT DOCUMENTS
2010/0204397 A1*  8/2010  Kobayashi

FOREIGN PATENT DOCUMENTS
CN            107216505 A  *  9/2017   ......... A41D 19/0062

OTHER PUBLICATIONS

Anna Dziemidkiewicz, etc., Metal Complexes as New Pro-Ecological Crosslinking Agentsfor Chloroprene Rubber Based on Heck Coupling Reaction, Jul. 1, 2019, Rubber Chemistry and Technology (2019) 92 (3): 589-597. (Year: 2019).*
Translation of CN107216505 (Year: 2017).*

* cited by examiner

*Primary Examiner* — Ling Siu Choi
*Assistant Examiner* — Huihong Qiao
(74) *Attorney, Agent, or Firm* — Greenberg Traurig, LLP

(57) ABSTRACT

A thermoplastic elastomeric formulation comprises (i) a water based thermoplastic elastomer (TPE), (ii) a surfactant, (iii) an antioxidant, (iv) a antifoaming agent and (v) a crosslinking agent. The water based TPE is styrene-isoprene-styrene (SIS) copolymer latex. A glove that is produced using the thermoplastic elastomeric formulation of the present invention is known as water based TPE gloves, such as water based TPE medical exam gloves, water based TPE household gloves and water based TPE industrial gloves in particular water based TPE surgical gloves.

12 Claims, No Drawings

THERMOPLASTIC ELASTOMERIC FORMULATION

CROSS-REFERENCE TO RELATED APPLICATION

This application claims priority under 35 U.S.C. § 119 to Malaysia Patent Application No. PI2019006282, filed Oct. 24, 2019, the disclosure of which is incorporated by reference herein in its entirety.

FIELD OF THE INVENTION

The present invention relates to a thermoplastic elastomeric formulation to produce a thermoplastic elastomer (TPE) product.

BACKGROUND OF THE INVENTION

Thermoplastic elastomers (TPE) are one of the most versatile plastics. Typically, thermoplastic elastomeric materials exhibit the properties of both plastics and rubbers as they are a physical mixture of polymers (a plastic and a rubber). The unique properties of both materials exist because TPE materials are created only by physical mixing of a thermoplastic and elastomer and no chemical or covalent bonding exists between both the materials. As such, TPE have become a significant part of the polymer industry. They are used in many applications like adhesives, footwear, medical devices, automobile parts, household goods, etc.

However, application of TPE in the production of elastomeric products does have its own disadvantages. For an example, for solvent based TPE glove production, solvent based latex dipping is required to breakdown the latex molecule arrangement into liquid form. Further, vulcanization and maturation hours are required to achieve reasonable tensile strength for various types of gloves such as nitrile gloves, polyisoprene gloves, polychloroprene gloves and natural rubber gloves but not limited thereto.

Having said the above, presently the existing approaches have their own disadvantages such as the approaches involve tedious steps, heavy chemicals consumption or are time consuming. As such, there is a need to identify a formulation which is suitable to overcome the above shortcomings. Hence, the present invention is targeted to produce water based TPE gloves which are able to overcome the above shortcomings.

SUMMARY OF THE INVENTION

The present invention relates to a thermoplastic elastomeric formulation that comprises (i) water based TPE, (ii) surfactant, (iii) antioxidant, (iv) antifoaming agent and (v) crosslinking agent. The water based TPE is styrene-isoprene-styrene (SIS) copolymer latex wherein the styrene is in a ratio of 15% to 35% and isoprene is in a ratio of 65% to 85%. The water based TPE is in an amount of 100 phr. The surfactant is any one selected from the group consisting of amphoteric surfactant such as monosodium N-Lauryl-betalminodipropionic acid or anionic surfactant such as sodium dodecylbenzene sulphonate, alkyldiphenyloxide disulphonate, dioctyl sulphosuccinates, and alkyl benzene sulphonate, preferably monosodium N-Lauryl-betalminodipropionic acid. The surfactant is in a range of 0.30 phr to 0.50 phr, preferably 0.40 phr. The antioxidant is any one selected from the group consisting of thiophenolic type antioxidant which is 2,6-di-tert-butyl-4-(4,6-bis(octylthio)-1,3,5-triazin-2-ylamino)phenol, poly(dicyclopentadiene-co-P-cresol), and alkylated diphenylamines, preferably 2,6-di-tert-butyl-4-(4,6-bis(octylthio) 1,3,5-triazin-2-ylamino)phenol. The antioxidant is in a range of 1.00 phr to 3.00 phr, preferably 2.00 phr. The antifoaming agent is any one selected from the group consisting of polydimethylsiloxane, emulsion of modified silicone, mixture of polypropylene based or polyether dispersion, preferably emulsion of modified silicone. The antifoaming agent is in a range of 0.02 phr to 0.06 phr, preferably 0.04 phr. The crosslinking agent is any one selected from the group consisting of bivalent or trivalent ionic compound, such as aluminium hydroxide, and zinc oxide, preferably zinc oxide. The crosslinking agent is in a range of 0.50 phr to 2.00 phr, preferably 1.50 phr. A glove that is produced using the thermoplastic elastomeric formulation of the present invention is known as water based TPE gloves, such as water based TPE medical exam gloves, water based TPE household gloves and water based TPE industrial gloves in particular water based TPE surgical gloves.

DETAILED DESCRIPTION OF THE INVENTION

A detailed description of preferred embodiments of the present invention is disclosed herein. It should be understood, however, that the embodiments are merely exemplary of the present invention, which may be embodied in various forms. Therefore, the details disclosed herein are not to be interpreted as limiting, but merely as the basis for the claims and for teaching one skilled in the art of the invention. The numerical data or ranges used in the specification are not to be construed as limiting.

The present invention relates to a water based thermoplastic elastomeric formulation that is free of an accelerator to produce a water based TPE product. Particularly, the present invention relates to a water based thermoplastic elastomeric formulation comprising water based TPE which is styrene-isoprene styrene copolymer (SIS) and a method of incorporating the water based TPE for manufacturing elastomeric product specifically water based TPE gloves, such as water based TPE medical exam gloves, water based TPE household gloves and water based TPE industrial gloves, in particular water based TPE surgical gloves.

The gloves produced in the present invention are accelerator free water based TPE gloves, in particular water based TPE surgical gloves which are produced using water based TPE latex. The TPE latex is a water-based copolymer material that involves a two-phase structure comprising styrene segment (plastic) and isoprene segment (elastomer/rubber) or known as styrene-isoprene-styrene (SIS) copolymer latex. Water based TPE latex is synthetic latex from a combination between styrene and isoprene monomers. There is no vulcanization and no maturation hours required to achieve reasonable tensile strength. However, crosslinking can be optionally included to improve the properties of the gloves. The monomer arrangement of water based TPE latex is slightly different from other types of latex. This is because it does not require any accelerator to produce a continuous film as has been applied in other types of available latex.

The main objective of the present invention is to provide water based TPE gloves, in particular water based TPE surgical gloves, without an accelerator. The other objective of the present invention is to provide water based thermoplastic elastomeric formulation that is capable of forming an elastomeric product with improved mechanical properties in comparison with solvent based TPE gloves.

The glove formulation comprises (i) a water based TPE, (ii) a surfactant, (iii) an antioxidant, (iv) an antifoaming agent and (v) a crosslinking agent.

The water based TPE is styrene-isoprene-styrene (SIS) copolymer latex wherein the styrene is in a ratio of 15% to 35% and isoprene is in a ratio of 65% to 85%. The water based TPE is in an amount of 100 phr.

The surfactant is any one selected from the group consisting of amphoteric surfactant such as monosodium N-Lauryl-betalminodipropionic acid or anionic surfactant such as sodium dodecylbenzene sulphonate, alkyldiphenyloxide disulphonate, dioctyl sulphosuccinates, and alkyl benzene sulphonate, preferably monosodium N-Lauryl-betalminodipropionic acid. The surfactant is in a range of 0.30 phr to 0.50 phr, preferably 0.40 phr.

The antioxidant is any one selected from the group consisting of thiophenolic type antioxidant which is 2,6-di-tert-butyl-4-(4,6-bis(octylthio)-1,3,5-triazin-2-ylamino)phenol, poly(dicyclopentadiene-co-P-cresol,) and alkylated diphenylamines, preferably 2,6-di-tert-butyl-4-(4,6-bis(octylthio)-1,3,5-triazin-2-ylamino)phenol. The antioxidant is in a range of 1.00 phr to 3.00 phr, preferably 2.00 phr.

The antifoaming agent is any one selected from the group consisting of polydimethylsiloxane, emulsion of modified silicone, mixture of polypropylene based or polyether dispersion, preferably emulsion of modified silicone. The antifoaming agent is in a range of 0.02 phr to 0.06 phr, preferably 0.04 phr.

The crosslinking agent is any one selected from the group consisting of bivalent or trivalent ionic compound, such as aluminium hydroxide, and zinc oxide, preferably zinc oxide. The crosslinking agent is in a range of 0.50 phr to 2.00 phr, preferably 1.50 phr.

Table 1 shows chemical components (as listed above) and compositions thereof used in preparing the water based TPE glove.

TABLE 1

Chemical components and compositions thereof used to prepare the water based TPE glove

| Chemical components | Preferred range (*phr) | Typical value (*phr) |
|---|---|---|
| Water based TPE | 100 | 100 |
| Surfactant | 0.30 to 0.50 | 0.40 |
| Antioxidant | 1.00 to 3.00 | 2.00 |
| Antifoaming agent | 0.02 to 0.06 | 0.04 |
| Crosslinking agent | 0.50 to 2.00 | 1.50 |

*parts per hundred of rubber

The following examples are constructed to illustrate the present invention in a non-limiting sense.

A former was dipped into the formulation as described in Table 1 using an available dipping process by controlling certain process parameters such as former temperature before latex dipping and curing condition in order to produce good quality water based TPE surgical gloves. The process parameters for the thermoplastic elastomeric formulation are tabulated in Table 2.

TABLE 2

Process parameters for water based TPE glove

| Process parameters | Preferred range | Typical value |
|---|---|---|
| Coagulant (Calcium nitrate) dipping | 12% to 18% | 15% |
| TPE compound (final TSC) | 28% to 32% | 30% |
| Former temperature before latex dipping | 50° C. to 60° C. | 55° C. |
| Curing temperature | 100° C. to 120° C. | 110° C. |
| Curing time | 18 min to 22 min | 20 min |

There were 4 sets of gloves being studied. Set A is water based TPE surgical glove (present invention), Set B is solvent based TPE surgical glove, Set C is polyisoprene (PI) surgical glove and Set D is natural rubber (NR) surgical glove. Gloves produced were tested for their mechanical properties such as tensile strength, elongation at break, modulus @ 500% and force at break. The results obtained are shown in Table 3 and Table 4.

TABLE 3

Mechanical properties of glove

| Set | | A | B | C | D | Standard requirement (ASTM 3577) |
|---|---|---|---|---|---|---|
| Weight, g | | 10.00 | 10.00 | 12.50 | 10.00 | |
| Thickness, mm | | 0.168 | 0.223 | 0.220 | 0.120 | |
| Tensile strength, MPa | Before aging | 25.42 | 18.71 | 20.45 | 26.20 | Min. 17 |
| | After aging | 18.59 | 18.41 | 18.51 | 28.05 | Min. 12 |
| Elongation at break, % | Before aging | 1228.82 | 977.65 | 924.00 | 839.24 | Min. 650 |
| | After aging | 1123.09 | 970.35 | 815.00 | 838.97 | Min. 490 |
| Modulus @ 500%, MPa | Before aging | 1.71 | 1.77 | 1.87 | 3.84 | Max. 7 |

Remarks:
Set A: Water based TPE surgical glove;
Set B: Solvent based TPE surgical glove;
Set C: PI surgical glove; and
Set D: NR surgical glove

TABLE 4

Force at break (FAB) properties of glove

| Set | Force at Break (FAB), N | |
| --- | --- | --- |
|  | Before Aging | After Aging |
| A | 9 to 10 | 11 to 12 |
| B | 15.32 | 14.79 |
| C | 10 to 11 | 10 to 12 |
| D | 7 to 10 | 8 to 10 |
| Standard requirement (EN455) | Median 9 | |

Remarks:
Set A: Water based TPE surgical glove;
Set B: Solvent based TPE surgical glove;
Set C: PI surgical glove; and
Set D: NR surgical glove Based on ASTM 3577 standard in Table 3, Set A has better tensile strength as 10 compared to Set B and Set C as well as comparable tensile strength with Set D before aging. Further, Set A has better elongation at break and softness (modulus @ 500%) than Set B, Set C and Set D. Set A have elongation at break of more than 1000%. This is because the lower the modulus, the softer the glove. The results showed that Set A having good mechanical properties as the conventional gloves such as Set B, Set C and Set D.

Further, the gloves prepared in the present invention do not contain protein content which eliminates Type I protein allergies. Further, lesser additives are added in the formulation as compared to surgical glove products using natural rubber (NR), acrylonitrile butadiene rubber (NBR), polychloroprene rubber (CR) and polyisoprene rubber (PI). The gloves prepared in the present invention also do not require any accelerator to be added in the formulation so Type IV allergies can be eliminated. Additionally, no vulcanization and no maturation hours are required to achieve reasonable tensile strength which reduces the manufacturing time and cost. Further, as TPE used in the present invention is water based TPE, it does not require dipping in a solvent.

The glove of the present invention may be used in a variety of applications such as but not limited to cleanroom, food handling, cosmetic, biomedical, semiconductor, electrical and/or healthcare. Additionally, teachings of the present invention are not limited to gloves as person skilled in the art can adopt the teachings of the present invention for any other elastomeric articles which exhibit similar elastomeric characteristics such as dental dams, condoms, finger cots, exercise band and the like products.

As a whole, the glove of the present invention, which is produced using water based TPE latex (i.e. SIS copolymer), is able to overcome the conventional shortcomings. For an example, no vulcanization and maturation hours are required to achieve reasonable tensile strength. Further, the manufacturing time and cost are reduced as well.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises", "comprising", "including" and "having" are inclusive and therefore specify the presence of stated features, integers, steps, operations, elements and/or components, but do not preclude the presence or addition of one or more other features, integers, steps, operations, elements, components and/or groups therefrom.

The method, steps, processes and operations described herein are not to be construed as necessarily requiring their performance in the particular order discussed or illustrated, unless specifically identified as an order of performance. It is also to be understood that additional or alternative steps may be employed. The use of the expression "at least" or "at least one" suggests the use of one or more elements, as the use may be in one of the embodiments to achieve one or more of the desired objects or results.

What is claimed is:

1. A thermoplastic elastomeric formulation that is free of an accelerator comprising:
   (i) a water based thermoplastic elastomer (TPE) in an amount of 100 phr,
   wherein the water based TPE is styrene-isoprene-styrene (SIS) copolymer latex;
   (ii) a surfactant in a range of 0.30 phr to 0.50 phr,
   wherein the surfactant is any one selected from a group consisting of an amphoteric surfactant and an anionic surfactant;
   (iii) an antioxidant in a range of 1.00 phr to 3.00 phr,
   wherein the antioxidant is any one selected from a group consisting of thiophenolic type antioxidant which is 2,6-di-tert-butyl-4-(4,6-bis(octylthio)-1,3,5-triazin-2-ylamino)phenol, poly(dicyclopentadiene-co-p-cresol) and alkylated diphenylamines;
   (iv) an antifoaming agent in a range of 0.02 phr to 0.06 phr,
   wherein the antifoaming agent is any one selected from a group consisting of polvdimethylsiloxane, emulsion of modified silicone, mixture of polypropylene based and polyether dispersion, and
   (v) a crosslinking agent in a range of 0.50 phr to 2.00 phr,
   wherein the crosslinking agent is any one selected from a group consisting of bivalent and trivalent ionic compound including aluminium hydroxide and zinc oxide.

2. The thermoplastic elastomeric formulation as claimed in claim 1, wherein the (SIS)copolymer latex having styrene in a ratio of 15% to 35% and isoprene in a ratio of 65% to 85%.

3. A glove having the thermoplastic elastomeric formulation as claimed in claim 2.

4. The glove as claimed in claim 3, wherein the glove is a water based TPE surgical glove.

5. The thermoplastic elasto eric formulation as claimed in claim 1, wherein the amphoteric surfactant is monosodium N-Lauryl-beta-Iminodipropionic acid.

6. A glove having the thermoplastic elasterneric formulation as claimed in claim 5.

7. The glove as claimed in claim 6, wherein the glove is a water based TPE surgical glove.

8. The thermoplastic elastomeric formulation as claimed in claim 1, wherein the anionic surfactant is any one selected from the group consisting of sodium dodecylbenzene sulphonate, alkyldiphenyloxide disulphonate, dioctyl sulphosuccinates and alkyl benzene sulphonate.

9. A glove having the thermoplastic elastomeric formulation as claimed in claim 1.

10. The glove as claimed in claim 9, wherein the glove is a water based TPE surgical glove.

11. A glove having the thermoplastic elastomeric formulation as claimed in claim 8.

12. The glove as claimed in claim 11, wherein the glove is a water based TPE surgical glove.

\* \* \* \* \*